United States Patent
Chee et al.

(10) Patent No.: US 6,315,757 B1
(45) Date of Patent: Nov. 13, 2001

(54) BRAIDED BODY BALLOON CATHETER

(75) Inventors: Uriel Hiram Chee, San Carlos; Erik T. Engelson, Menlo Park; Gene Samson, Milpitas, all of CA (US)

(73) Assignee: Target Therapeutics, Inc., Fremont, CA (US)

(*) Notice: Subject to any disclaimer, the term of this patent is extended or adjusted under 35 U.S.C. 154(b) by 0 days.

(21) Appl. No.: 09/314,568

(22) Filed: May 19, 1999

Related U.S. Application Data

(63) Continuation of application No. 08/607,847, filed on Feb. 27, 1996, now Pat. No. 5,906,606, which is a continuation-in-part of application No. 08/566,802, filed on Dec. 4, 1995, now abandoned.

(51) Int. Cl.[7] .................................................. A61M 29/00
(52) U.S. Cl. ........................ 604/103.09; 604/527; 604/524
(58) Field of Search ..................................... 604/523, 524, 604/527, 264, 96.01, 103.09; 600/435, 433; 606/192, 194

(56) References Cited

U.S. PATENT DOCUMENTS

| | | | |
|---|---|---|---|
| 3,174,854 | * | 3/1965 | Buehler et al. . |
| 3,351,463 | * | 11/1967 | Rozner et al. . |
| 3,753,700 | * | 8/1973 | Harrison et al. . |
| 4,723,936 | * | 2/1988 | Buchbinder et al. . |
| 4,932,959 | * | 6/1990 | Horzewski et al. . |
| 4,976,689 | * | 12/1990 | Buchbinder et al. . |
| 4,981,478 | * | 1/1991 | Evard et al. ........................ 604/282 |
| 5,234,416 | * | 8/1993 | Macaulay et al. . |
| 5,250,069 | * | 10/1993 | Nobuyoshi et al. .................. 606/192 |
| 5,254,107 | * | 10/1993 | Soltesz . |
| 5,267,979 | * | 12/1993 | Appling et al. . |
| 5,290,230 | * | 3/1994 | Ainsworth . |
| 5,304,198 | * | 4/1994 | Samson . |
| 5,338,295 | * | 8/1994 | Cornelius et al. . |
| 5,364,354 | * | 11/1994 | Walker et al. . |
| 5,364,357 | * | 11/1994 | Aase . |
| 5,429,597 | * | 7/1995 | DeMello et al. . |
| 5,437,632 | * | 8/1995 | Engelson . |
| 5,445,624 | * | 8/1995 | Jimenez ................................ 604/280 |
| 5,451,209 | * | 9/1995 | Ainsworth et al. . |
| 5,454,795 | * | 10/1995 | Samson . |
| 5,462,523 | * | 10/1995 | Samson et al. . |
| 5,531,721 | * | 7/1996 | Pepin et al. . |
| 5,533,987 | * | 7/1996 | Pray et al. . |

(List continued on next page.)

FOREIGN PATENT DOCUMENTS

| | | |
|---|---|---|
| 2103001 | 8/1996 | (CA) . |
| 0 205 851 | * 12/1986 | (EP) . |
| 0 358 117 | 3/1990 | (EP) . |
| 2 172 205 | * 9/1986 | (GB) . |
| 2233562 | 1/1991 | (GB) . |
| 235347 | 10/1993 | (TW) . |
| WO 93/20881 | 10/1993 | (WO) . |
| WO 94/27668 | 12/1994 | (WO) . |
| WO 95/23626 | 9/1995 | (WO) . |

Primary Examiner—Anhtuan T. Nguyen
Assistant Examiner—Cris L. Rodriguez
(74) Attorney, Agent, or Firm—Morrison & Foerster LLP

(57) ABSTRACT

This is a balloon catheter having braided layer which extends generally from the proximal end of the catheter to a location distal of the balloon. In particular, it is desirable that the shaft of the catheter proximal of the balloon be stiffest at the proximal section and least stiff just proximal of the balloon. Although the catheter may be a single lumen catheter using some type of a core wire to act as a valve for inflation and deflation of the balloon, it is within the scope of the invention to include either a separate inflation/deflation lumen or one incorporated into the various concentric polymeric layers used to make up the proximal shaft. Particularly preferred is the use of an elastic, compliant balloon.

5 Claims, 6 Drawing Sheets

U.S. PATENT DOCUMENTS

| | | | |
|---|---|---|---|
| 5,676,659 | * | 10/1997 | McGurk et al. . |
| 5,683,410 | * | 11/1997 | Samson .................................. 606/194 |
| 5,728,063 | * | 3/1998 | Preissman et al. . |
| 5,728,065 | * | 3/1998 | Follmer et al. . |
| 5,755,708 | * | 5/1998 | Segal . |
| 5,782,811 | * | 7/1998 | Samson et al. ....................... 604/282 |
| 5,820,613 | * | 10/1998 | Van Werven-franssen et al. 604/282 |
| 5,843,050 | * | 12/1998 | Jones et al. . |
| 6,176,871 | * | 1/2001 | Pathak et al. ............................. 623/1 |
| 6,186,978 | * | 2/2001 | Samson et al. .................... 604/96.01 |
| 6,193,686 | * | 2/2001 | Estrada et al. ................... 604/103.09 |
| 6,217,565 | * | 4/2001 | Cohen .................................. 604/525 |

* cited by examiner

BRAIDED BODY BALLOON CATHETER

RELATED APPLICATIONS

This is a continuation of application Ser. No. 08/607,847, filed Feb. 27, 1996, U.S. Pat. No. 5,906,606, which was a continuation-in-part of application Ser. No. 08/566,802, filed Dec. 4, 1995, now abandoned, the entirety of which is incorporated by reference.

FIELD OF THE INVENTION

This invention is a surgical device. In particular it is a balloon catheter having a braided layer which extends generally from the proximal end of the catheter to a location distal of the balloon. In particular, it is desirable that the shaft of the catheter proximal of the balloon be stiffest at the proximal section and least stiff just proximal of the balloon. Although the catheter may be a single lumen catheter using a core wire acting as a valve for inflation and deflation of the balloon using that single lumen, it is within the scope of the invention to include either a separate inflation/deflation lumen or one isolated from the central lumen and incorporated into the various coaxial layers used to make up the catheter. Particularly preferred is the use of an elastic, compliant balloon which may be inflated and deflated through the lumen provided for that purpose. Catheters having "leaky" balloons are also suitable in this invention.

BACKGROUND OF THE INVENTION

This invention relates generally to a highly flexible catheter having a balloon at its distal tip. The form of the catheter is such that it may be used in various percutaneous transluminal angioplasty (PTA) procedures but is sufficiently flexible in its construction that it may be used for other diagnostic and treatment indications in regions of the body having significantly more tortuous vasculature.

For instance, in PTCA procedures, a guiding catheter typically having a preshaped distal tip is introduced into the vasculature of a patient. The catheter is advanced from the entry point, up into the aorta and, once at that site, is twisted or torqued from the proximal end of the catheter so to turn the preshaped distal tip of the guiding catheter in to the ostium of a desired coronary artery. A balloon-bearing or "dilatation" catheter is then advanced through the lumen of a guiding catheter and is progressed out the guiding catheter's distal tip until the balloon on the distal extremity of the dilatation catheter extends cross the region to be dilated. The balloon is then expanded, typically to a predetermined size dictated by the design of the balloon, via the use of radioopaque liquid at relatively high pressures. Upon completion of the procedure, the balloon is then deflated so that the dilatation catheter can be removed and blood flow resumed through the thus-treated artery.

In other procedures, a balloon-bearing catheter typically of a somewhat smaller diameter than a catheter used in PTA or PCTA might be used. In a universal sense, the procedure might be considered to be similar in that a larger or guiding catheter is initially placed so that its distal end is near the body site to be treated or diagnosed. The balloon-catheter, perhaps with the guidewire through an existing central lumen, would then be extended from the distal end of the guiding catheter to the site. the balloon is expanded and once the procedure is complete, the balloon is deflated and removed from the body. In some instances, the balloon might be of a compliant nature rather than the fixed diameter configuration found in a typical PTA balloon.

The advent of interventional radiology as a viable alternative in neurological regions of the body have produced demands on catheterization equipment not faced by demands placed on PTCA devices. The need for significantly smaller diameter devices, devices having a variable flexibility, ability to resist kinking (particularly in those regions where the differences in flexibility may be acute) is notable.

One way to produce strong catheter shafts for a balloon catheter is via the use of braids in those shafts. For instance, U.S. Pat. No. 5,338,295, to Cornelius et al. describes a dilatation balloon catheter having a shaft formed of a tubular stainless steel braid. The proximal outer tube section is encased in a polyimide material. The distal outer tube section which forms the balloon is made of a polymeric material such as polyethylene. The braid in this instance extends only partially down the proximal portion of the catheter. It does not extend as far as the balloon nor does it extend through the balloon.

Another similar device is shown in U.S. Pat. No. 5,451,209, to Ainsworth et al. Ainsworth et al. describes a composite tubular element useful in intravascular catheters. In particular it is shown as an element, variously of a fixed wire dilatation catheter and in a guiding or angiographic catheter. The structure of the device is made by braiding strands from a mixture of a polymeric matrix materials (such as fibers or powders) having a relatively low melting point and a high strength reinforcing fiber having a relatively high melting point. The fibers are woven into a tubular element; the resulting braided tubular element is heated to melt the low melting point matrix material so as to flow around the reinforcing fibers to form a matrix. Thermoplastic jackets or coatings are then extruded or otherwise applied to the exterior of the thus-produced braided tubular element. There is no suggestion in the patent to either produce a shaft which has variable stiffness proximally nor to use only a metallic braid from the proximal end of a over the wire catheter to a position distal of the balloon.

U.S. Pat. No. 5,429,597 to DeMello, teaches a balloon catheter which is said to be kink resistant. In general, it appears to be made up of an outer polymeric covering over a "cross-wound multifilar (CWMF)" coil and a non-fixed, removable core wire. The CWMF coil is a pair of helical coils which are wound in opposite directions to provide for torque transmission during use. There appears to be no suggestion of weaving the CWMF into a braid. There is no suggestion of extending the CWMF through the length of the balloon interior.

The PCT application to Pray et al. (WO 93/20881) assigned to Scimed Medical Systems suggests a dilatation catheter having a shaft with a proximal section which is a composite of polymeric material and a stainless steel braid tube. The distal section of the catheter is formed of a flexible polymeric tube. In one embodiment of the described device, the braid weave of the proximal section of the shaft has a varying pick count, increasing in the distal direction, thereby providing for increased flexibility in the distal direction. However, this document does not suggest the use of a braided tube extending distally of the balloon. Furthermore, there is no suggestion of the use of an elastomeric or rubbery balloon on the device.

Published UK Patent Application G.B. 2,233,562A, by Hannam et al., shows a balloon catheter having a flexible, hollow inner shaft and an outer braided shaft with a balloon inflated by fluid introduced between the inner and outer shafts. The inner shaft is fixed relative to the outer shaft at both ends. When the balloon is inflated, the outer shaft shortens. The excess length of the inner shaft is accommodated via the inner shaft bending into a coil-like form. The braid is said typically to be of a fabric of a polyester floss. It is said to extend the entire length of the outer shaft but with a varying pick rate apparently in the neighborhood of the balloon. The balloon is made of the material of the loose braided layer and a flexible, elastic polyurethane. There is no suggestion of using the braided material as an overall stiffener in the balloon catheter device. There is no suggestion of placing the braid on the interior of the balloon.

None of the published documents teaches the inventive balloon catheter.

SUMMARY OF THE INVENTION

This invention is a catheter used for insertion into some lumen of the human body. In general, it may be used in a vascular lumen but is suitable for treatment of other body lumen as may be found in the genito-urinary systems, the biliary system, or wherever else a remotely controllable balloon is desired.

The physical structure of the inventive balloon catheter includes a braid of either ribbon or wire, which extends generally from the proximal end of the catheter to a region on the distal end of the catheter assembly, preferably distal of the balloon. Typically, the braid has a polymeric tubing member externally and internally, both adjacent the braid member. The polymers of those adjacent tubing members may fill the interstices of the braid member or an adhesive may be used if so desired. In a preferred variation, the openings in the braided tubular member may function as a fluid passageway between the inner lumen of the catheter into the balloon itself. Further, in a most desirable aspect of this invention, the braid acts as a stiffener both at the region just proximal of the balloon and for the balloon itself. This is especially useful when the catheter is of the type having decreasing stiffness between the proximal end of the catheter and a point just proximal of the balloon.

The catheter most desirably has an inner layer of lubricious polymeric tubing. The inner lubricious layer may extend all the way to the distal tip or may extend into the region just proximal and distal of the proximal end of the balloon. This helps somewhat with stiffness and kinking control at the critical proximal end of the balloon. The catheter, when it is a single lumen catheter having an open distal end, may include passageways from the inner lumen through the inner lubricious layer and braid into the balloon. As noted above, if the inner lubricious layer does not extend completely through the interior of the balloon, the inflation fluid may pass radially through the braid wall.

When the balloon catheter is a single lumen catheter, it is quite desirable that the portion just distal of the balloon be fitted with a valve seat in its lumen so to cooperate with a valve seat found on a core wire or guide wire. In this way, the user of the balloon catheter may introduce the inflation fluid through the single lumen into the balloon and inflate that balloon merely by seating the core wire's valve member onto the valve seat provided in the catheter lumen.

Another variation of this invention includes the provision of cast or extruded passageways in the outer surface of inner lubricious tubing so that the passageways are in communication with the balloon. In this way, the balloon may be inflated and deflated using these ancillary openings and yet the inner central passageway may be used for a number of other purposes.

Finally, the balloon member used in this inventive catheter assembly may be either elastomeric and radially compliant to provide for a variety of functions not typically attempted by use of a polyethylene balloon.

The concept of this inventive balloon catheter is the provision of a highly flexible, highly compliant balloon catheter which is amenable to use in very distal vasculature. It is designed in such a way that in spite of the fact that it has very high flexibility, it is also quite resistant to kinking, particularly in the region just proximal of the balloon.

DESCRIPTION OF THE INVENTION

Figure 1:
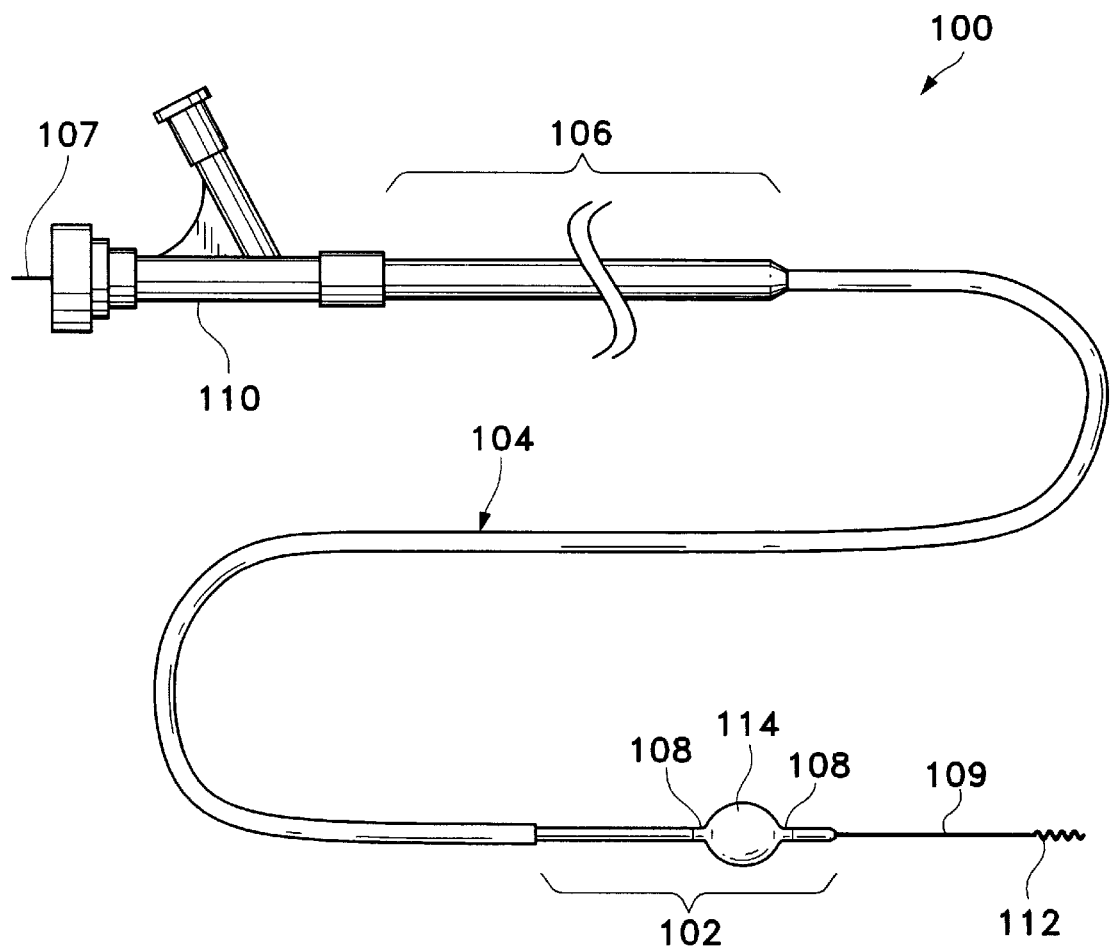
FIG. 1 shows a plan view of one highly desirable variation of an overall assembly of the invention.

FIG. 1 shows a side view of a catheter assembly, generally designated (100), made according to the invention. The catheter assembly (100) comprises an elongate tubular member with a balloon section (102) at the distal end of the catheter, body section (104) proximal of balloon section (102), and a proximal section (106). The catheter assembly (100) is designed generally for operation in combination with a flexible guide-wire (109) preferably with a bendable guiding tip (112) which is often a coil. The guide-wire is used to guide the catheter assembly (100) along complicated and tortuous pathways typically in the human vasculature to a target site within the body. The design of guidewire (109) may be of any convenient design which allows manipulation of the combined catheter (100) and the guidewire (109) to the desired site. The overall length of the catheter assembly is typically between 30 cm and 175 cm, depending on the portion of the body to be reached by the catheter (100) through the chosen body access site. For instance, if the chosen site is within the brain and the femoral artery in the groin is the access site, the length of the catheter (100) would be in the higher regions of noted range. If the access is through the neck, as would be the case with significantly obese patients, the overall length of the catheter can be much shorter.

At the proximal end of the catheter device (100) is shown an end fitting (110) through which the guidewire may be received and through which fluid material may be introduced into the catheter lumen. One suitable fitting has an axially extending port through which the guidewire is rotated and advanced or retracted axially within the catheter, during a catheter placement operation. A side port may be used to deliver other fluid materials through the catheter to the target site potentially after removal of the guidewire.

One concept central to this particular invention is to be noted in that the portion of the catheter assembly (100)

which is proximal of balloon (114) typically is of stepped or staged flexibility. That is to say that proximal section (106) is stiffer than mid-section (104), which in turn is stiffer than the portion of balloon section (102) which is found proximal of balloon (108). In a very general sense, this sequence of flexibilities allows a catheter such as shown here to follow the increasingly more narrow vasculature as the catheter is progressed within the body from the entrance point to the target site within the body. Although three sections of different flexibility are shown here, it is not necessary that the number of sections be only three. It may be four or six or ten, depending upon the needs of the designer providing for the detailed variation of this catheter and the needs of the attending physician in introducing it to the human body. Indeed, it may be that one or more of the sections may be continuously variable in flexibility as a function of the axial length. For instance, it might be highly desirable to have a proximal section (106) which is of a single flexibility so to allow ease of pushability and access through a guiding catheter and yet have mid-section (104) and balloon section (102) be continuously variable in stiffness. That the proximal section is significantly stiffer than the portion of the balloon section (102) proximal of the balloon is significant to this invention.

The balloon (114), as was noted above, is shown in balloon section (102). The presence of the balloon is obviously central to this invention.

Figure 2A:
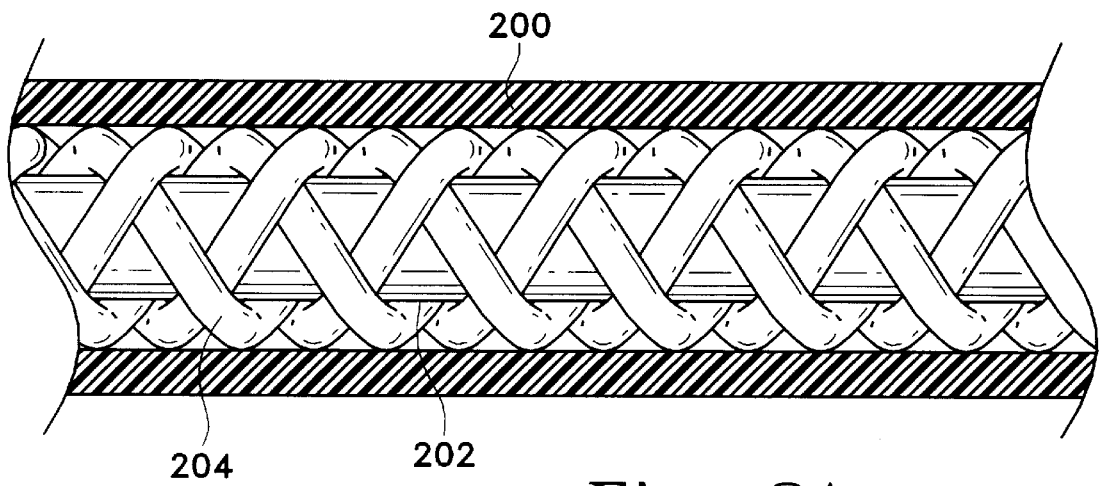
FIG. 2A shows a partial cutaway of the shaft portion of the inventive catheter showing a wire type braid.
Figure 2B:
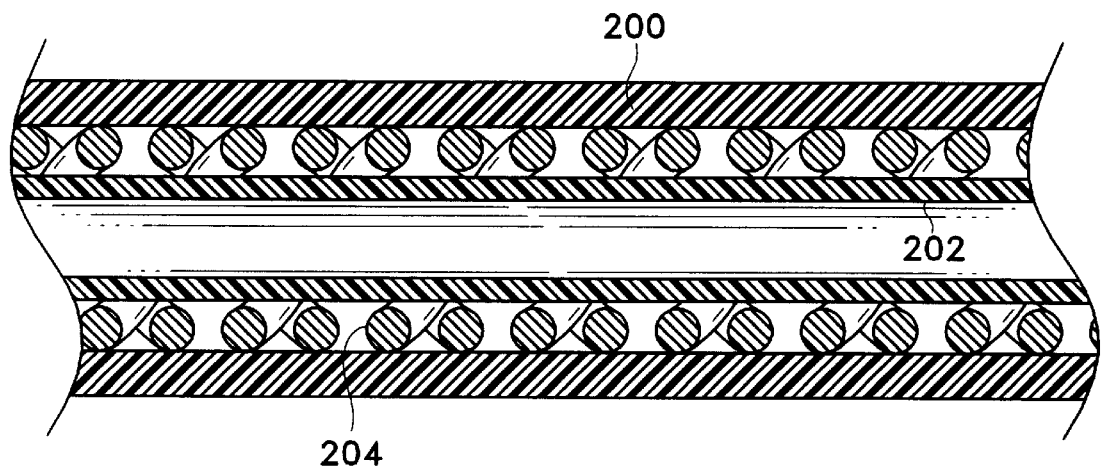
FIG. 2B shows a full cutaway of the FIG. 2A depiction.

Also central to this invention is the use of a braided layer positioned within the wall of the catheter assembly (100). FIG. 2A shows a partial cutaway side view of a section of the inventive catheter (100) which is proximal of the balloon (114) (see FIG. 1). In this cutaway may be seen an outer covering (200), an inner liner (202) and the braid (204) positioned between the two layers. FIG. 2B shows the structure in greater detail because of its full cutaway depiction. The outer covering (200) is again shown in cross-section. The inner liner (202) and the wires making up braid (204) are shown in cross-section. As shown in FIG. 2, both outer covering member (200) and inner member (204) are polymeric. They are desirably selected of materials which tack to each other upon heating. They may also be melt-miscible. In some instances, they may contain components which act in the manner of adhesives, but such is not necessary. Typically, for the simple variation shown in FIGS. 2A and 2B, the outer covering member (200) is of a material which may be heat-shrinkable onto the inner member (202) and the braid member (204). Preferred polymeric materials for the outer layer (200) include such materials as polyethylene, polyvinyl chloride (PVC), ethylvinyl acetate (EVA), polyethylene terephthalate (PET), and polyurethane, and their mixtures and block or random copolymers. Clearly, such materials as PVC and polyurethane are not of the type which are heat-shrinkable onto the outer layer of the catheter section. Other methods may be chosen to place these materials on the outer section of the catheter. One such procedure involves slipping the inner section (202) and braid (204) onto a mandrel of appropriate size to support the diameter of the inner section. A length of tubing of a material suitable for the outer covering member (200) and a heat-shrinkable tubing exterior is then slipped over the combination of the inner section (202), braid (204), mandrel. Upon selection of the proper temperature-dependent physical parameters of the respective polymers. the heat-shrink tubing may be used to squeeze a polymeric material—e.g., polyurethane—onto the braid (204) when the heat-shrink temperature is above the glass transition temperature of the outer layer (200). The heat-shrinkable tubing may then be stripped off before further assembly of the catheter or, obviously, before use.

Another useful class of polymers are thermoplastic elastomers, including those containing polyesters as components. Typical of this class is materials sold as Hytrel. Additionally, an adhesive may be coated onto the inner liner tubing. Polyesters and polyimides, in particular, care useful as adhesives on its surface.

Inner liner (202) is a thin (preferably less than about 0.0015 inches) tubing of a lubricious polymer such as a polyfluorocarbon. Although a wide variety of materials are generically suitable in the service, thin layers may be made of polytetrafluoroethylene (PTFE) or fluoroethylene polymers (FEP). This inner liner (202) runs generally from the proximal portion of the catheter assembly (100 in FIG. 1) to some point at least just proximal of the balloon (114 in FIG. 1). The fluoropolymers may be etched to provide a surface to which other polymers may adhere. The outer covering member (200) may be treated or heated so to allow penetration of the polymer in the outer covering member (200) through the openings in the braid and allow such adherence.

It should be noted that each of the polymers described herein may be doped or filled with radio-opaque materials such as barium sulfate, bismuth trioxide, bismuth carbonate, powdered tungsten, powdered tantalum or the like so that the location of various portions of the catheter sections may be radiographically visualized as present in the human body.

Figure 3A:
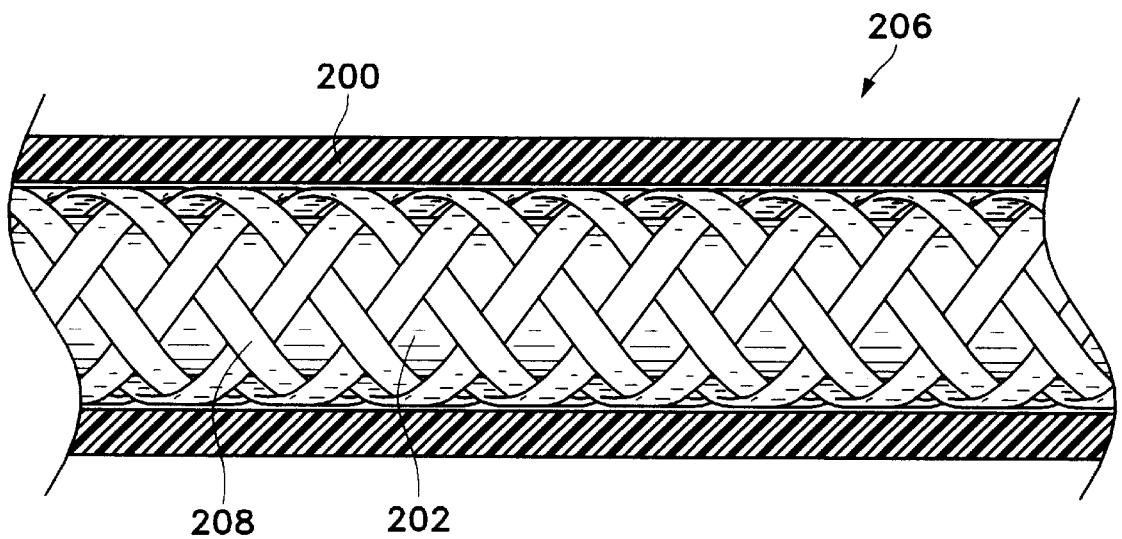
FIG. 3A shows a partial cutaway, side view of a catheter shaft made according to the invention using a ribbon type braid.

FIG. 3A shows another catheter section (206) having an outer covering (200), an inner liner (202), and a braid (208). In this case, the braid is constructed of a flat ribbon of a metal or alloy rather than the wire-shaped braid members shown in FIGS. 2A and 2B. Similarly, FIG. 3A shows a full cross-section of the catheter section (206) with an outer covering (200), an inner lubricious tubular member (202) and the braided member (208) in a cross-section.

As should be apparent from this description, it is within the scope of this invention to have multiple polymeric layers exterior of the braid (204 or 208), as well as of multiple polymeric liner members interior to braid (204 or 208). Furthermore, it is within the scope of the invention to include multiple braids and/or flat ribbon coils between or amongst the various polymeric layers.

It is also within the scope of this invention to coat at least one of the exterior surfaces of outer member (200) with a lubricious coating, whether such coating is chemically bonded to the layer or is merely physically coated onto the relevant surface. A description of suitable procedures for producing such lubricious coatings is found in U.S. patent application Ser. No. 08/060,401 ("LUBRICIOUS CATHETERS"), filed May 12, 1993; U.S. patent application Ser. No. 08/235,840 ("METHOD FOR PRODUCING LUBRICIOUS CATHETERS"), filed Apr. 29, 1995; and U.S. patent application Ser. No. 08/272,209 ("LUBRICIOUS FLOW-DIRECTED CATHETER"), filed Jul. 8, 1994, the entirety of which are incorporated by reference.

Figure 3B:
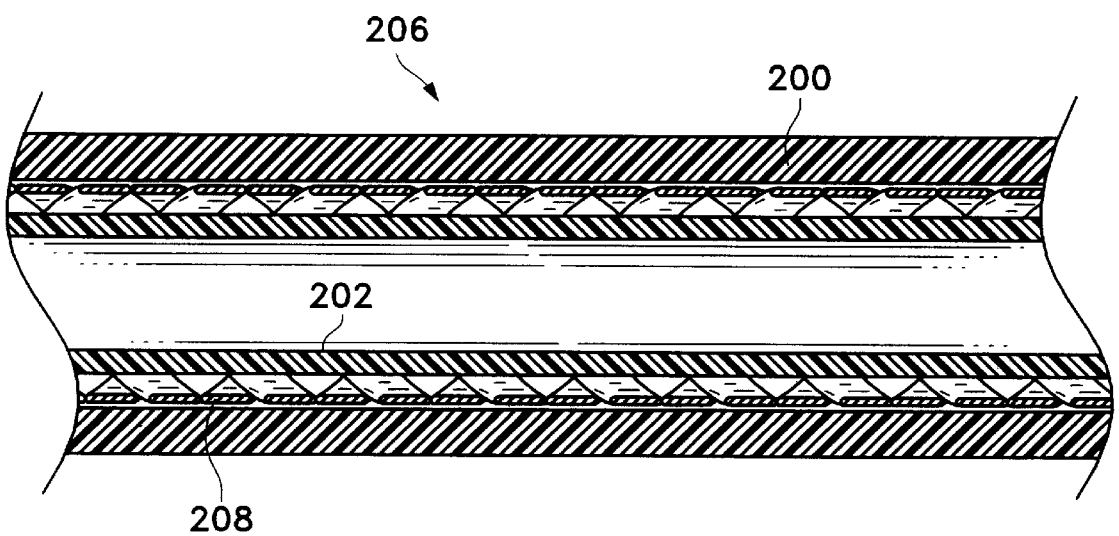
FIG. 3B shows a full cutaway of the FIG. 3A depiction.

The metallic braid shown in FIGS. 2A, 2B, 3A, and 3B is preferably made up of a number of metallic ribbons, as shown in FIGS. 3A and 3B, although wire-based braids, as shown in FIGS. 2A and 2B are also acceptable if a site diameter penalty is acceptable. Preferably a majority of the metallic ribbons are wires in braids (204) or (208) are members of a class of alloys known as super-elastic alloys.

Preferred super-elastic alloys include titanium/nickel alloys, particularly materials known as nitinol—alloys which were discovered by the U.S. Naval Ordnance Laboratory. These materials are discussed at length in U.S. Pat. No. 3,174,851 to Buehler et al., U.S. Pat. No. 3,351,463 to Rozner et al. and U.S. Pat. No. 3,753,700 to Harrison et al. Commercial alloys containing some amount, commonly up to about 5%, of one or more other members of the iron group, e.g., Fe, Cr, Co, etc., are considered to be encompassed within the class of super-elastic Ni/Ti alloys suitable for this service. When using a braid containing some amount of a super-elastic alloy, an additional step may be desirable to preserve the shape of the stiffening braid. For instance, with a Cr-containing Ni/Ti superelastic alloy which has been rolled into 1×4 mil ribbons and formed into a 16-member braid, some heat treatment is desirable. The braid may be placed onto a, e.g., metallic, mandrel of an appropriate size and then heated to a temperature of 600 degrees to 750 degrees for a few minutes, to set the appropriate shape. After the heat treatment step is completed, the braid retains its shape and the alloy retains its super-elastic properties.

Other materials which are suitable for the braid include stainless steels (303, 308, 310 and 311).

Metallic ribbons (208) that are suitable for use in this invention desirably are between 0.25 mil and 3.5 mil in thickness and 2.5 mil and 12.0 mil in width. By the term "ribbon", we intend to include elongated cross-sections such as a rectangle, oval, or semi-oval. When used as ribbons, these cross-sections should have an aspect ratio of thickness-width of at least 0.5.

It is within the scope of this invention that the ribbons or wires making up the braid also be of materials other than super-elastic alloys. A minor amount of fibrous materials, both synthetic and natural, may also be used. In certain applications, particularly in smaller diameter catheter sections, more malleable metals and alloys, e.g., bold, platinum, palladium, rhodium, etc., may be used. A platinum alloy with a few percent of tungsten is sometimes preferred partially because of its radio-opacity.

Suitable nonmetallic ribbons or wires include materials such as those made of polyaramides (Kevlar), polyethylene terephthalate (Dacron), or carbon fibers. The braids used in this invention may be made using commercial tubular braiders. The term "braid" is meant to include tubular constructions in which the ribbons making up the construction are woven in an in-and-out fashion as they cross, so as to form a tubular member defining a single lumen. The braid members may be woven in such a fashion that 2–4 braid members are woven together in a single weaving path. Typically, this is not the case. It is much more likely that a single-strand weaving path, as is shown in FIGS. 2A and 3A is used.

The braid shown in FIGS. 2A and 3A has a nominal pitch angle of 45 degrees. Clearly the invention is not so limited. Other braid angles from 20 degrees to 60 degrees are also suitable. One important variation of this invention is the ability to vary the pitch angle of the braid either as the braid is woven or at the time the braid is included in catheter section or sections. In this way, the braid itself may be used to vary the flexibility of various sections of the catheter.

Figure 4:
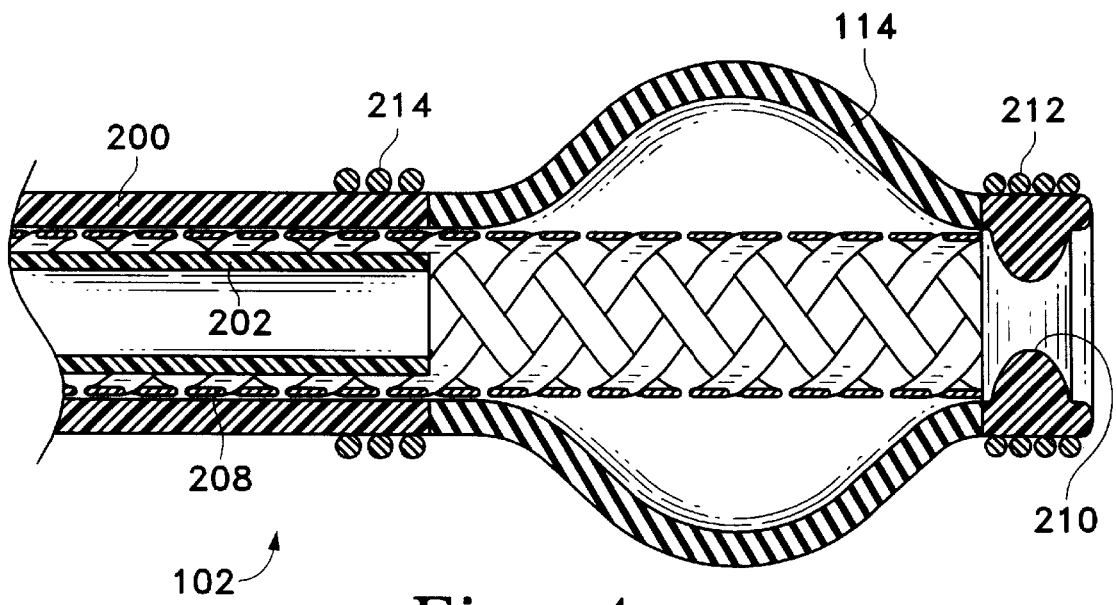
FIGS. 4 and 5 show cutaway, side views of two variations of the inventive balloon catheter.

FIG. 4 shows the distal tip of catheter such as shown in FIG. 1 in cross-section. In this variation, the outer covering element (200) is shown abutting balloon (114). As was noted above, the end of the inner liner (202) extends distally of the most proximal portion of the catheter and terminates just at the edge of balloon (114). The braid member (in this case ribbon braid (208)) also extends from some site approximately of the balloon to terminate near the distal end of balloon (114). The braid has a number of functions in this and the following variations. In particular, it stiffens the balloon (114) itself and at least in this instance serves as the passageway for fluid flow between the lumen of braid (208) and the balloon (114). This openings between the ribbons of the ribbon braid (208) also allow for deflation of the balloon. Control of the inflation fluid is achieved by the use of valve seat (210). The inner radius of valve seat (210) is a size to engage cooperatively a ball or other appropriate shape placed on a guide wire or core wire in a manner known in the prior art. As the valving is engaged either distally or proximally on valve seat (210) (depending on whether the control wire is inserted from the distal end or the proximal end of the catheter) the single opening for releasing the fluid from the catheter is closed and any additional fluid introduced into the lumen of the catheter itself will inflate the balloon (114). The balloon may be deflated using reverse of that procedure. Also shown in FIG. 4 is a distal radio-opaque marker (212) and a proximal radio-opaque marker (214). These two markers (212 and 214) are shown to be coils for ease of display. They may also be bands or other markers known in the art. Markers of this type are typically made of materials such as those listed above, e.g., platinum, gold, and various related alloys. These markers are individually optional in this invention. Other means are known for locating the position the balloon at the distal end of the catheter.

As noted above, one of the major reasons for carrying the braid member (208) from the proximal end of the balloon down through the distal end of the balloon (114) is to assure that the joint between the portion of section (102) just proximal of the balloon and the balloon itself is strengthened. Kinking often occurs proximally of the balloon because of the difference in stiffness between the balloon (114) and its proximal neighbor section.

The balloon (114) itself is desirably produced from elastomeric material. Many balloons used on balloon catheters are produced of material such as polyethylene. Polyethylene balloons are not elastomeric. Such balloons are merely folded axially to accommodate passage of the distal tip of the catheter assembly through a guiding catheter and then through narrow curvatures in the vasculature. It is difficult to bend such a folded balloon and consequently it is not always as maneuverable as it desirably could be. An elastomeric balloon, on the other hand, is simply inflatable. It need not be folded. The catheter design described here is suitable for any size of catheter, but for use in very narrow portions of the vascular, the axial length of the balloon should be between 2 mm and 10 mm. The non-expanded diameter may be between 0.035 inches and 0.064 inches for neurosurgical devices. For other uses, the distal end of the catheter (100) may be 0.120 inches or larger. The elastomeric balloon (114) is preferably of a material such as natural or synthetic rubbers, silicones, polyurethanes, and their block or random copolymers. One especially useful class of materials are elastomeric urethane copolymers, e.g., polyurethane/polycarbonate thermoplastics such as Carbothane sold by Thermedics. Adhesives may be used to seal the balloon (114) against the outer tubing covering (200). A polymeric hydrophilic coating over the balloon (114) and the inner surfaces of inner tubing (202) may be desirable.

The balloon section (102) is perhaps the most flexible portion of the catheter assembly and typically comprises about five to 35% of the overall length of the catheter assembly (100).

Figure 5:
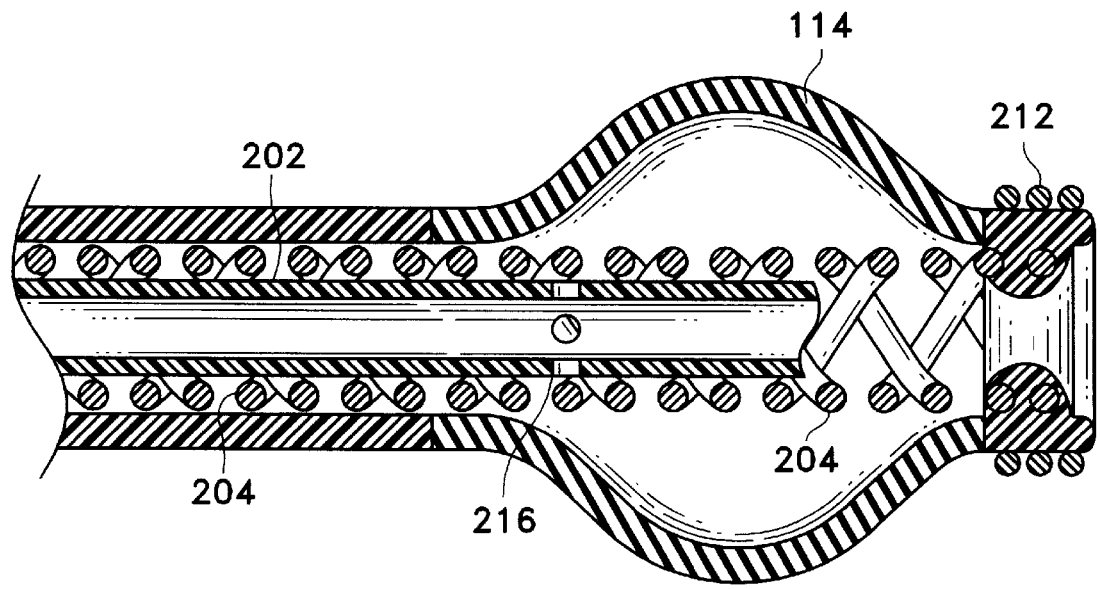

FIG. 5 shows another variation of distal tip of the inventive catheter in which the braid (204) is based on wire rather than ribbon and the inner lubricious liner (202) extends to some position interior of the balloon (114). This provides some additional stiffening to the overall design in the more distal portion of the inventive device. The radio-opaque marker (212) is displayed distally to the balloon (114) and is shown as a single presence. No matching or complimenting radio-opaque marker is found proximally of balloon (114). The variation shown in FIG. 5 are merely for the purpose of depicting differences and not for limiting the noted structure in any way. A braid based on a ribbon may just as well be used in this variation. Additional radio-opaque markers may also be used. Also shown in this variation is the presence of several holes in the wall of the inner liner (202). These holes (216) permits additional passage of fluid from the interior of the inner lubricious tubing (202) into the balloon (114).

Figure 6A:
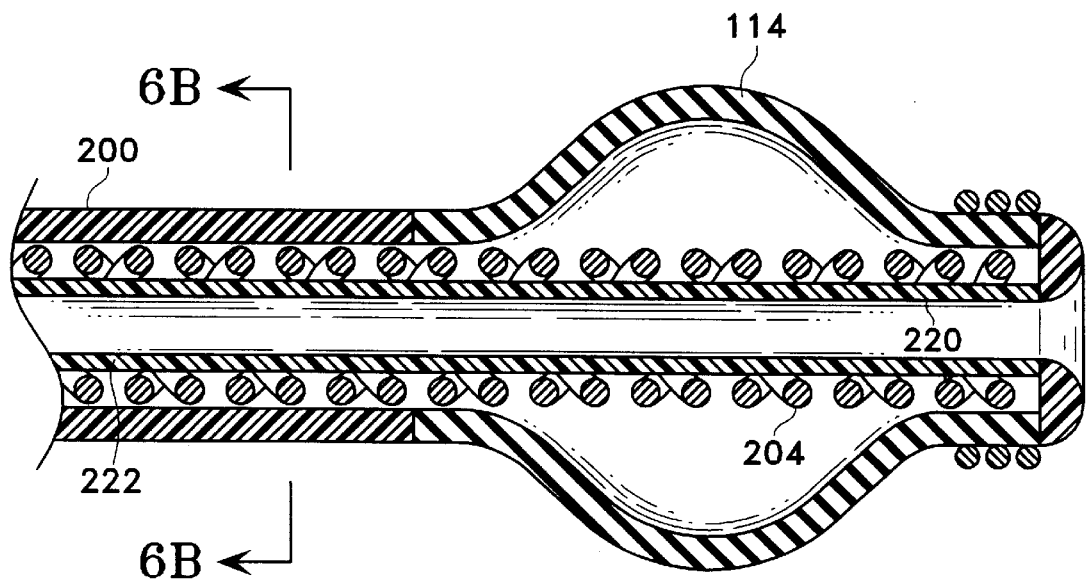
FIG. 6A shows a cutaway, side view variation of the distal end of the inventive catheter.
Figure 6B:
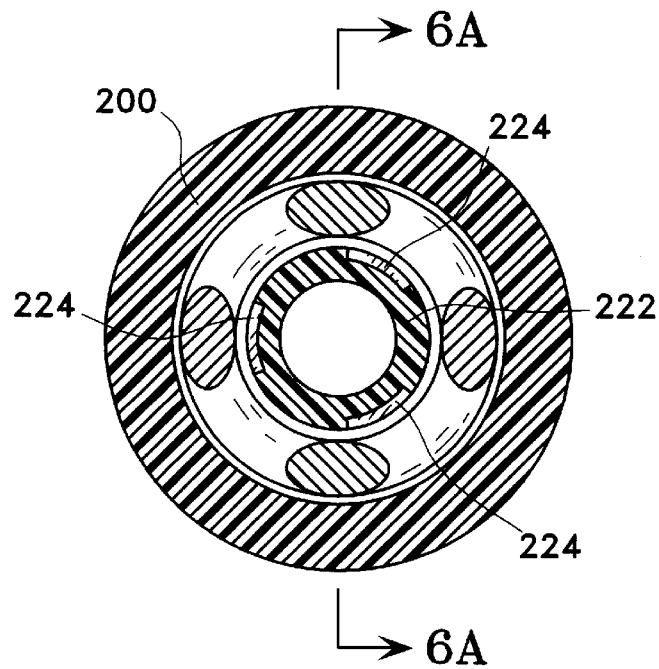
FIG. 6B shows a cross section of the shaft of the FIG. 6A variation showing the inflation lumens placed at the outer surface of the inner lubricious layer.

FIGS. 6A and 6B show a significantly different variation of the inventive catheter assembly. In this variation, the distal-most portion of the catheter is without a valve seat of the type shown in FIGS. 4 and 5. In this variation, the inner lumen (220) of the catheter is not in fluid communication with the balloon (114). The inner lubricious tubing section (222) is sealed at the distal tip of the catheter. This variation is shown with a wire type braid (204) but as above, a ribbon braid may be used in its stead. The balloon is inflated using one or more inflation lumens (224) found in liner (222). Fluid passes through the inflation lumens (224) from the proximal end of the catheter assembly through the interstices between the turns and weaves of the braid into the balloon (114). Deflation is carried out by use of the same fluid passageway or passageways. This design provides for unfettered use of the central lumen (220) without interference with a guide wire. High fluid flow catheters would desirably be of this design.

Figure 7:
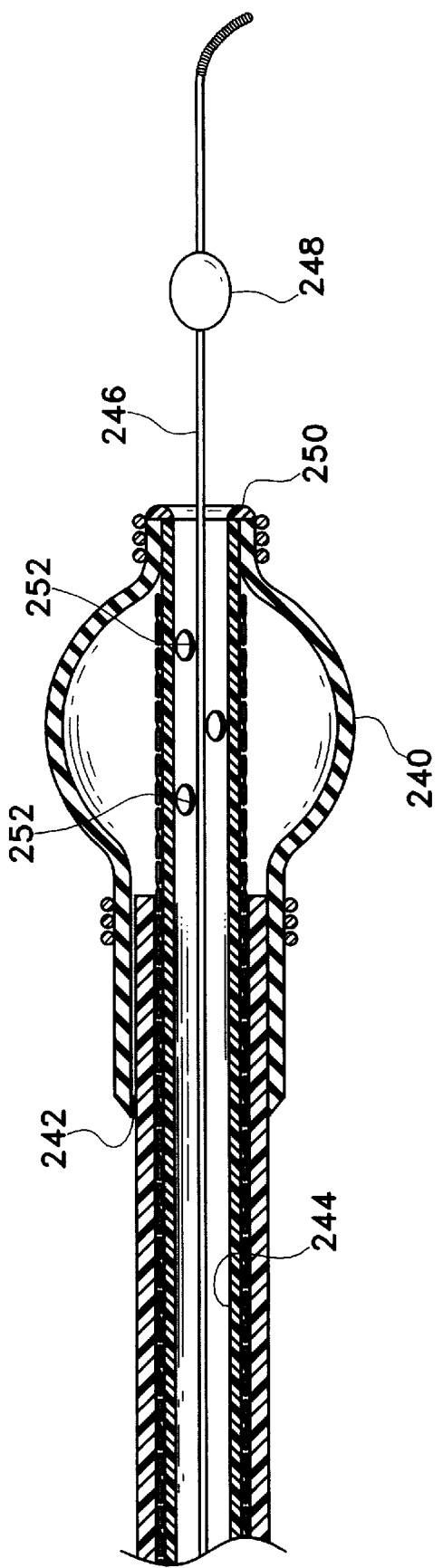
FIG. 7 shows a cutaway, side-view of a "leaker" balloon suitable for use in this inventive catheter.

FIG. 7 shows another variation of the inventive catheter. In this instance, the balloon (240) has one or more orifices (242) which serve as "leakers" to allow the fluid filling the balloon (240) to leak slowly from the interior. This variation of the catheter assembly is designed primarily to hasten access of the catheter tip to a selected treatment site. The central lumen (244) is designed to accommodate a guidewire (246) having a valve member (248) situated external to the distal tip of the catheter assembly. As the guidewire (246) is withdrawn proximally, the valve member (248) fits against the tip (250) of the catheter and seals against the catheter. Fluid injected into the lumen (244) of the catheter passes through the passageways (252) provided and into the balloon (240). The balloon (240) inflates. Once inflated, the holes (242) allow the fluid to pass slowly into the body lumen. This combination of catheter is especially effective in accessing remote sites because the balloon acts as a sail, the size of which may be modulated by coordination of the fluid introduction and leak rate. The speed of the combination is caused thus: the balloon is used when a high flow region in the vasculature is encountered; the balloon is deflated and the guidewire is used to select one branch of a bifurcated pathway when the selected pathway does not evidence the higher flow. The braided shaft located in the proximal section allows the physician to push with the confidence that the catheter will follow the chosen path without kinking at any point.

Many alterations and modifications may be made by those of ordinary skills in the art without departing from the spirit and scope of this invention. The illustrated embodiments have shown only for purposes of clarify. The examples should not be taken as limiting this invention as defined by the following claims which claims includes all equivalents, whether those equivalents are now or later devised.

We claim as our invention:

1. A balloon catheter assembly comprising:
    a) an elongate tubular member having a distally located balloon portion having an inflatable balloon and a proximally located shaft portion having a proximal end and a distal end and a lubricious inner liner member,
    b) a central lumen extending through both said balloon portion and said shaft portion and wherein said central lumen is not in fluid communication with said inflatable balloon, and
    c) a woven braided member extending from the shaft portion proximal end to a point located distally of the balloon portion
    wherein the lubricious inner liner member has an inner lumen forming the balloon catheter assembly central lumen and has an inflation passageway defined in an outer surface, the inflation passageway in fluid communication with the balloon portion, and
    wherein an inner surface of the braided member is contiguous to the outer surface of the lubricious inner liner member such that the braided member is disposed exteriorly to the inflation passageway.

2. The balloon catheter of claim 1 wherein said outer surface of said central lumen defines more than one inflation passageway in fluid communication with the balloon portion.

3. The balloon catheter assembly of claim 1, wherein the woven braided member extending from the shaft portion proximal end to a point located distally of the balloon portion is in fluid communication with the balloon portion.

4. The balloon catheter assembly of claim 1, wherein the lubricious inner liner member extends distally of the balloon portion.

5. The balloon catheter assembly of claim 4, wherein the woven braided member extending from the shaft portion proximal end to a point located distally of the balloon portion is in fluid communication with the balloon portion.

* * * * *